United States Patent
Couture et al.

(10) Patent No.: US 9,436,866 B2
(45) Date of Patent: Sep. 6, 2016

(54) HIGH SENSITIVITY FLAT PANEL MICROBIOLOGY DETECTION AND ENUMERATION SYSTEM

(71) Applicant: General Electric Company, Schenectady, NY (US)

(72) Inventors: Aaron Judy Couture, Schenectady, NY (US); Faisal Ahmed Syud, Clifton Park, NY (US); John Brian Hewgley, Schenectady, NY (US); Yu Zhao, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 230 days.

(21) Appl. No.: 14/449,916

(22) Filed: Aug. 1, 2014

(65) Prior Publication Data
US 2016/0034745 A1 Feb. 4, 2016

(51) Int. Cl.
*G06K 9/00* (2006.01)
*G06T 7/00* (2006.01)

(52) U.S. Cl.
CPC ......... *G06K 9/00127* (2013.01); *G06T 7/0012* (2013.01); *G06T 2207/10056* (2013.01); *G06T 2207/10064* (2013.01)

(58) Field of Classification Search
None
See application file for complete search history.

(56) References Cited

U.S. PATENT DOCUMENTS

| | | | | |
|---|---|---|---|---|
| 5,644,188 A * | 7/1997 | Potter | ...................... | H01J 3/022 313/308 |
| 6,075,578 A * | 6/2000 | Hayashi | ............... | G09G 3/3662 313/518 |
| 7,582,415 B2 | 9/2009 | Straus | | |
| 7,727,471 B2 | 6/2010 | Hsieh et al. | | |
| 9,090,462 B2 * | 7/2015 | Straus | ................... | B82Y 20/00 |
| 2003/0082516 A1 * | 5/2003 | Straus | ................... | B82Y 20/00 435/4 |
| 2006/0051816 A1 * | 3/2006 | Hsieh | ..................... | G01N 33/58 435/7.9 |
| 2013/0028379 A1 * | 1/2013 | Nelson | .................. | G01N 23/04 378/62 |
| 2013/0149738 A1 | 6/2013 | Bolea et al. | | |
| 2013/0316363 A1 | 11/2013 | Wainwright et al. | | |
| 2013/0323745 A1 | 12/2013 | Wainwright et al. | | |
| 2014/0091235 A1 * | 4/2014 | Iguchi | ...................... | G01T 1/20 250/487.1 |

OTHER PUBLICATIONS

Heeger et al., "Making Sense of Polymer-Based Biosensors," PNAS, Oct. 26, 1999, vol. 96, No. 22, pp. 12219-12221.
Kalkhoran, "Thin Film CdZnTe Detector Arrays for Digital Mammography," Dec. 2000.

(Continued)

*Primary Examiner* — Shefali Goradia
(74) *Attorney, Agent, or Firm* — Ziolkowski Patent Solutions Group, SC; Jean K. Testa

(57) ABSTRACT

A flat panel imaging system for imaging cells provided on a cell medium is disclosed. The system includes a housing having a base portion and a lid that collectively form a closed environment to exclude external sources of light, and a flat panel detector encased in the base portion and having an array of pixels each including a photodiode and transistor. The system also includes a first light source that illuminates cells on the cell medium to excite at least a portion of the cells and cause those cells to generate photons that are captured by the array of pixels and a second light source to illuminate cells on the cell medium with a light different from the light from the first light source and that provides for a capturing of photons representative of photons transmitted through the cells on the cell medium.

20 Claims, 7 Drawing Sheets

(56) References Cited

OTHER PUBLICATIONS

Johnson et al., "Early Detection and Measurement of Urothelial Tumors in Mice," Urology, Jun. 2006, vol. 67, No. 6, pp. 1309-1314.

Missbach-Guentner et al., "Flat-Panel Detector-Based Volume Computed Tomography: A Novel 3D Imaging Technique to Monitor Osteolytic Bone Lesions in a Mouse Tumor Metastasis Model," Evaluation Studies, Journal Article, Research Support, Sep. 2007, vol. 9, No. 9, pp. 755-765.

Tredwell et al., "Imaging Arrays for Medical Applications," RIT Quantum Limited Detector Workshop, Mar. 2009, pp. 1-106.

* cited by examiner

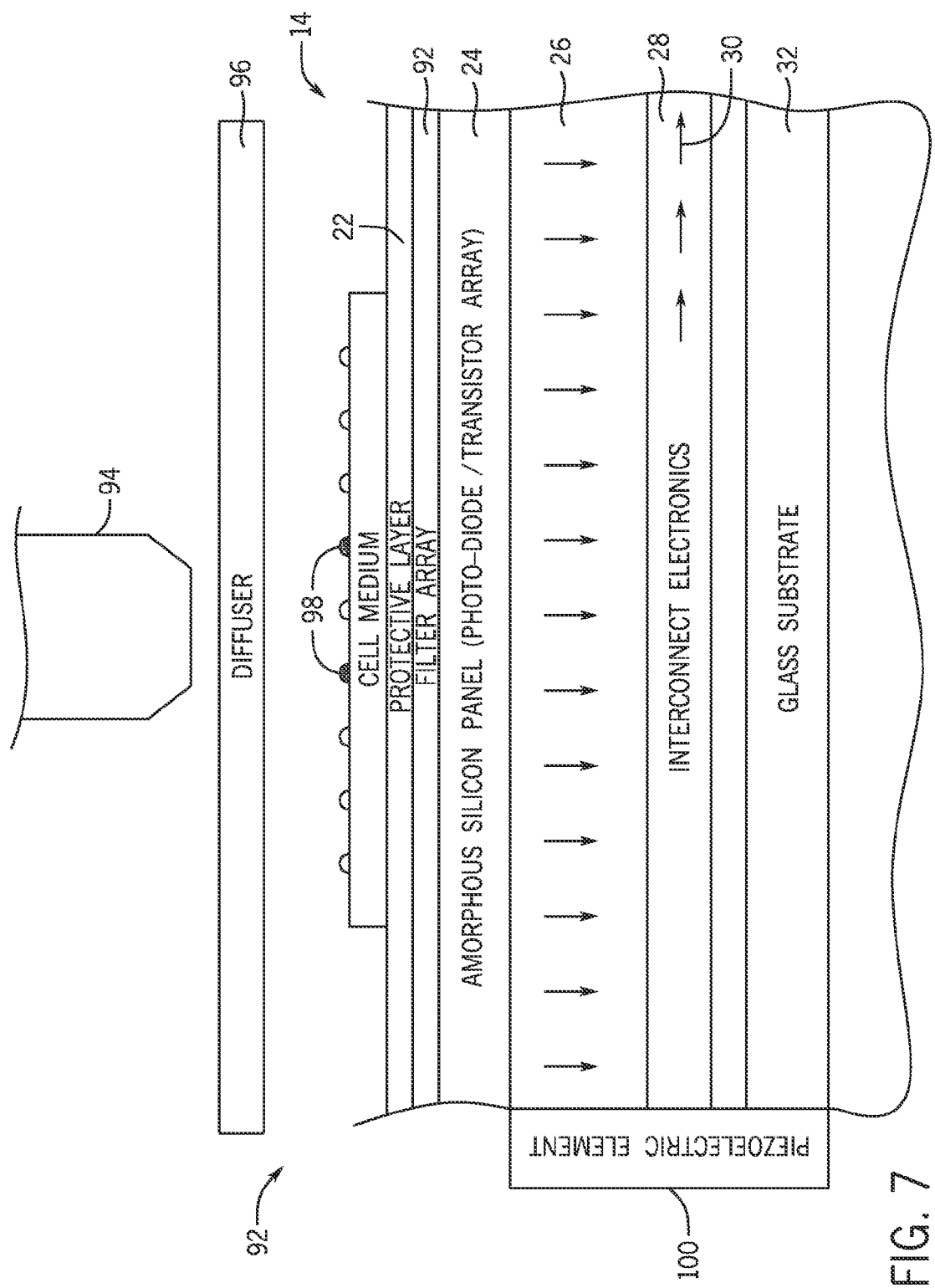

HIGH SENSITIVITY FLAT PANEL MICROBIOLOGY DETECTION AND ENUMERATION SYSTEM

BACKGROUND OF THE INVENTION

Embodiments of the invention relate generally to the detection, enumeration, and identification of replicating cells, especially microbial cells, and, more particularly, to a flat panel imaging system for acquiring digital images of microbial samples.

Microbial culture is the predominant methodology for the detection, enumeration, and identification of replicating cells, especially microbial cells (e.g., bacteria, yeasts, and molds), in medical, industrial, and environmental samples. Microbial culture provides for the detection of small numbers of microbes, as it allows for the simple visual detection of microbes by exploiting their propensity to reproduce in large numbers rapidly. A related microbial culture technique, called microbial enumeration or colony counting, quantifies the number of microbial cells in a sample. The microbial enumeration method, which is based on in situ microbial replication, generally yields one visually detectable "colony" for each microbial cell in the sample. Thus, counting the visible colonies—either manually by eye or thru an electronic/automated method—allows microbiologists to determine the number of microbial cells in a sample accurately. To perform microbial enumeration, bacterial cells can be dispersed on the surface of nutrient agar in petri dishes ("agar plates") and incubated under conditions that permit in situ bacterial replication. The individual, visually undetectable, microbe replicates repeatedly to create a large number of identical daughter microbes at the physical site where the progenitor microbial cell was deposited. The daughter cells remain co-localized (essentially contiguous) with the original cell, so that the cohort of daughter cells (which may grow to tens or hundreds of millions of cells) eventually form a visible colony on the plate.

In addition to quantifying the number of microbial cells in a sample via microbial enumeration or colony counting, it is often desired to perform additional analysis on microbial cells in the sample. For example, potential treatments and administering of medicine (i.e., antibiotics) to the cells may often be performed to analyze the effectiveness of the medicine in treating the cells. Such analysis is often performed in conjunction with a technique that allow for image capture of the sample—such as by employing fluorescent detection or chemiluminescent detection. In employing one of these techniques, the cells are stained with a fluorescent or chemiluminescent dye to activate or tag cells of interest. The fluorescent or chemiluminescent dye stained cell is excited by light and the emission of the excitation is then detected by a photosensor (e.g., a charge coupled device (CCD) camera) or film emulsion that captures a digital image of the sample and allows further data analysis.

The performing of fluorescent detection, chemiluminescent detection, and/or colorimetric detection according to existing techniques—specifically with respect to the use of film emulsion, complementary metal-oxide-semiconductor (CMOS) imagers, and/or CCD cameras to capture images—presents some drawbacks and limitations. For example, film emulsion is the conventional detection medium for chemiluminescent detection, but is characterized by non-linear response and limited dynamic range requiring multiple exposures, thereby resulting in a time-consuming and expensive imaging procedure. As another example, as chemiluminescent signals generated are normally weak and time-varying, relatively fast exposure (e.g., on the order of a minute), low noise, and high light detection efficiency is required for accurate image capture when using CCDs. Thus, limitations of the CCDs regarding operation at a low frame rate (due to the inherent sequential read-out thereof) and low temperature (to achieve a reasonable noise level) present challenges in accurately capturing the chemiluminescent signals. Still further, CCDs require a high efficiency optical lens to focus the large blot to small CCD chips (~1 $cm^2$)—with the optical lens adding to the cost of the high-end CCDs, increasing the size and vertical space of the imaging device (due to the large working distance of the CCD camera), and also causing problems with regard to light collection efficiency (due to the large working distance). Yet still another drawback of image capture via CCD is that the capturing of images can take approximately 3-20 minutes—depending on the desired exposure.

Other more recent attempts to provide a system that captures a digital image of the blot include a C-digit system released by LICOR Biosciences that utilizes a linear scanner with sixteen linear sensors. The linear scanner combines short working distance (like film emulsion) to maximize light collection efficiency and multiple small low cost linear sensor arrays to meet the data acquisition time requirement, but the scan time to scan the large area is still around multiple minutes per pass (i.e., 6-12 minutes). Additionally, there is a concern that during the scanning time (on order of 10 minutes), the transient behavior of the chemiluminescence in the blot itself will be changing. As such—as the linear scan is happening—the intensity at the beginning of the scan will be higher than the intensity of at the end of the scan (bottom of the scan), therefore introducing an artificial gradient in the measurement.

Regardless of the exact technique employed to provide an image capture of cells in a sample, it is recognized that such image capture is performed separately from the microbial enumeration or colony counting. That is, presently, there is no single system that provides for image capture and microbial enumeration in a "multi-tasking" environment, where a single system can provide for the performing of both tasks in a time efficient and effective manner.

Therefore, it would be desirable to provide a system that provides for both image acquisition of microbial cells in a sample and the enumeration of such cells—that overcomes the aforementioned drawbacks of conventional imaging techniques and associated systems. It would also be desirable for such a system to provide improved performance in regards to sensitivity, dynamic range, exposure time, and quantum efficiency, over a large acquisition area, while eliminating costly high-efficiency imaging optics such as are used with existing CCD image sensors, so as to provide a system at a reduced cost and size.

BRIEF DESCRIPTION OF THE INVENTION

In accordance with one aspect of the invention, a flat panel imaging system for imaging cells provided on a cell medium includes a housing having a base portion and a lid that collectively form a closed environment to exclude external sources of light from entering the housing and a flat panel detector encased in the base portion, the flat panel detector comprising an array of pixels each including a photodiode and transistor that convert photons received thereby to electrical signals that are representative of the photons impacting individual the respective pixel. The flat panel imaging system also includes a first light source configured to illuminate the cells on the cell medium with a light that excites at least a portion of the cells and causes those cells to generate photons that are captured by the array of pixels and a second light source configured to illuminate the cells on the cell medium with a light different from the light from the first light source, the light from the second light source providing for a capturing of photons by the array of pixels representative of photons transmitted through the cells on the cell medium.

In accordance with another aspect of the invention, a method for detecting and enumerating cells in a cell culture using a flat panel imaging system includes providing a cell medium having a plurality of cells thereon and placing the cell medium on a flat panel detector of a flat panel imaging system, the flat panel detector comprising an array of photodiodes and transistors that collect light generated from or transmitted through the cell medium. The method also includes collecting light emitted by cells on the cell medium responsive to an excitation of the cells achieved via one of a chemiluminescence imaging technique and a fluorescence imaging technique, the light emitted by the cells being collected by the array of photodiodes of the flat panel detector and converted to electric charges to generate a first set of light data. The method further includes processing the first set of light data to generate a first digital image of the cells, collecting light transmitted through the cells on the cell medium responsive to illumination of the cells by a light source integrated into the flat panel imaging system and via the array of photodiodes of the flat panel detector and converted to electric charges to generate a second set of light data, and processing the second set of light data to generate a second digital image of the cells.

In accordance with yet another aspect of the invention, a flat panel imaging system for detecting and enumerating cells microbial cells provided on a cell medium includes a housing having a base portion and a lid that collectively form a closed environment to exclude external sources of light from entering the housing and a flat panel detector encased in the base portion, the flat panel detector comprising an array of pixels each including a photodiode and transistor that convert photons received thereby to electrical signals that are representative of the photons impacting individual the respective pixel. The flat panel imaging system also includes a fluorescent light source configured to illuminate the cells on the cell medium so as to excite at least a portion of the cells and cause those cells to generate photons that are captured by the array of pixels and a white light source configured to illuminate the cells on the cell medium, with photons transmitted through the cells being captured by the array of pixels. The flat panel imaging system further includes an image reconstructor configured to process the electrical signals that are representative of the photons received by the array of pixels so as to provide for generation of a digital image of the cells on the cell medium, wherein the image reconstructor is configured to generate a first image of the microbial cells that captures cells that are excited responsive to illumination with the fluorescent light, with the first image tagging locations at which photons generated by cells excited responsive to illumination with the fluorescent light as containing a marked cell, and generate a second image of the microbial cells that captures cells through which photons are transmitted when illuminated by the white light source, the second image providing a total cell count of the microbial cells on the cell medium.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings:

FIG. 7 is an exploded sectional view of a flat panel imaging system, according to an embodiment of the invention.

DETAILED DESCRIPTION

Embodiments of the invention relate generally to molecular imaging and, more particularly, to a flat panel imaging system for acquiring digital images of microbial cells in a sample, so as to provide for the detection and enumeration of cells in such samples. The flat panel imaging system is a two-dimensional light sensitive image detector array which provides a digital image of the light collected on the detector surface. According to embodiments of the invention, the flat panel imaging system may be specifically constructed to function under chemiluminescence, absorbance (colorimetric), and fluorescence imaging modes, and/or combinations thereof.

Figure 1:
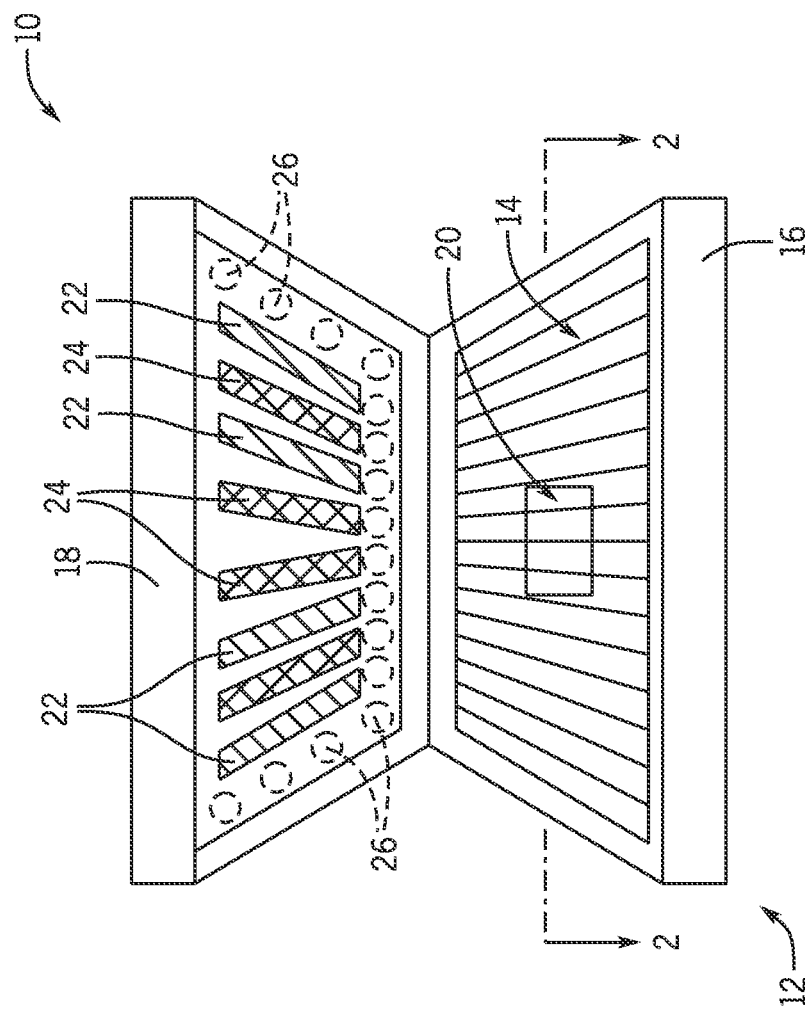
FIG. 1 is an elevated perspective view of a flat panel imaging system, including a flat panel detector, according to an embodiment of the invention.

Referring to FIGS. 1-4, a flat panel imaging system 10 for use in an image acquisition of microbial cells is provided according to an embodiment of the invention. FIG. 1 provides an elevated perspective view of the flat panel imaging system 10 generally including an outer housing 12 that houses a flat panel detector 14 therein to surround and protect the physical light receptors, electronic detection equipment and associated electronics of the flat panel detector 14. The outer housing 12 includes a base portion 16 that encases the flat panel detector 14 and a lid 18 that, according to one embodiment, is hinged to the base portion 16 so as to be selectively opened and closed with respect to the base portion to provide a "closed environment" to exclude external sources of light for performing of a microbial cell image acquisition. According to embodiments of the invention, the lid 18 may be formed as an opaque lid or a reflective lid—depending on the type of light source incorporated into the imaging system 10.

The flat panel detector 14 of the flat panel imaging system 10 functions as the light detection device in the image acquisition of microbial cells in a sample provided in/on a suitable cell medium 20—such as an agar plate that serves as a growth medium—that is placed directly onto the imaging surface of the flat panel detector 14. Photons are generated during the image acquisition via fluorescent detection, chemiluminescent detection, and/or colorimetric detection, with these photons being directly and efficiently collected from the sample. The flat panel detector 14 provides a digital image of light collected on the detector surface, with the digital image being a quasi-stationary image with desirable signal-to-noise ratio. The size of the flat panel detector—which may have dimensions of up to approximately 40×40 cm—allows for image acquisition of a large area cell medium 20, such as a 20×20 cm cell medium, for example.

In order to provide for light collection on the surface of the flat panel detector 14, the flat panel imaging system 10 includes transillumination light sources 22, 24 that provide illumination for performing of fluorescence imaging and/or colorimetric imaging when desired. In the embodiment of FIG. 1, a fluorescent light source 22 and a white light source 24 are incorporated into the lid 18 of the housing 12. The fluorescent light source 22—in the form of an ultraviolet (UV) light source or colored light source (e.g., red/green/blue (RGB) light source or blue light source)—is used in conjunction with a light-activated fluorescent stain or reagent to generate a light emission from cells in the sample 20—so as to tag cells/locations of interest and provide for enumeration of such cells. The white light source 24 provides illumination for the performing of colorimetric imaging, with a light absorption through the cell medium being measured to differentiate areas where cells are present or not present, in order to provide for estimation of a total cell count.

According to one embodiment of the invention, and as shown in phantom in FIG. 1, a uniform edge-lit LED panel 26 may also be provided in flat panel imaging system 10 that provides even lighting throughout the imaging area. The edge-lit LED panel 26 could have multiple pixels printed so that the color of the panel can be changed electronically and selected to best match the fluorescent (or chemiluminescent) dye being used at the moment.

Figure 2:
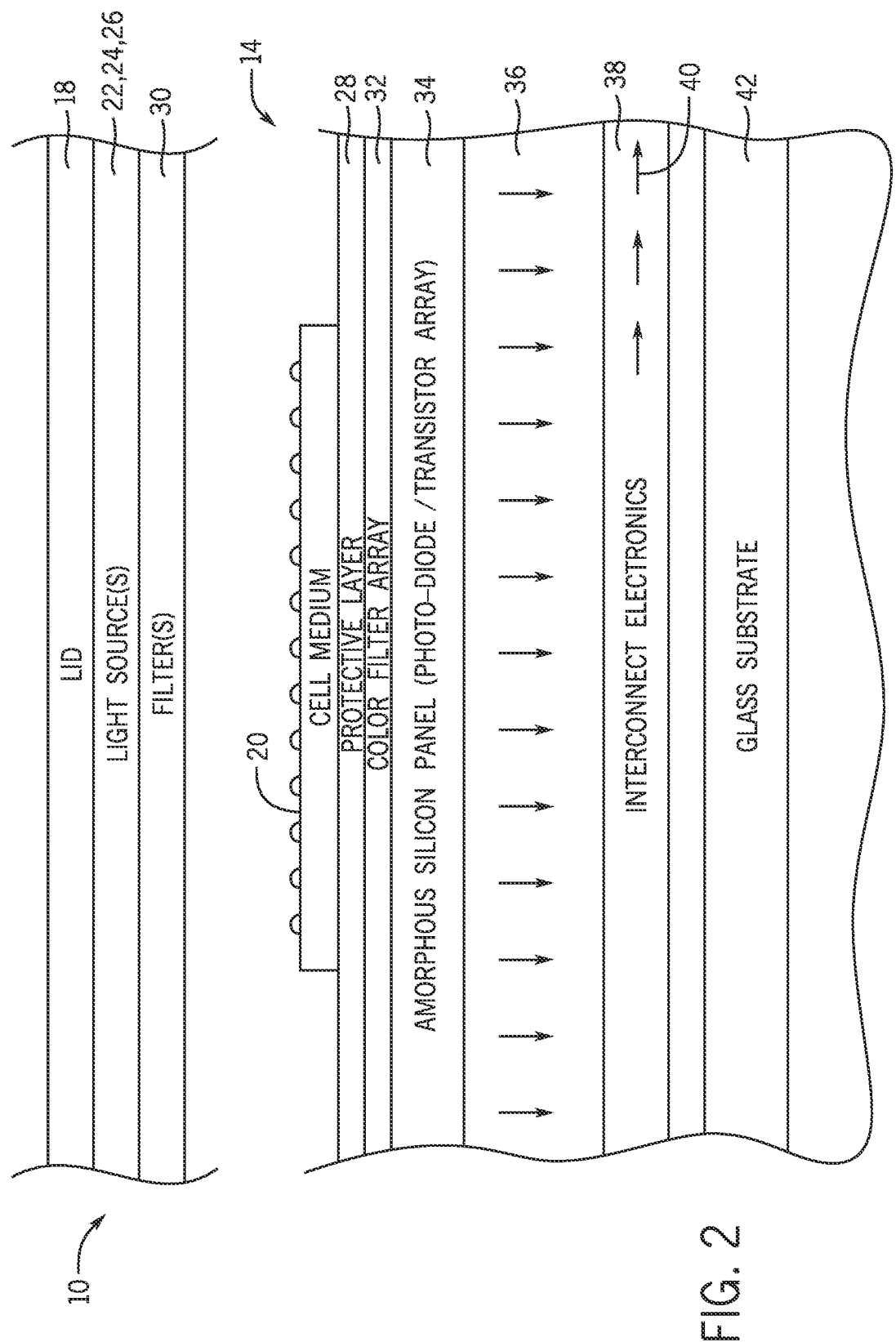
FIG. 2 is an exploded sectional view of the flat panel imaging system of FIG. 1 taken along line II-II, according to an embodiment of the invention.

Referring now to FIG. 2, an exploded sectional view of the flat panel imaging system 10 taken along line II-II of FIG. 1 is provided to better illustrate a construction thereof. As shown therein, light source(s)—i.e., fluorescent light input 22, white light 24 and/or edge-lit LEDs 26—are positioned adjacent lid 18 to provide illumination as need for a fluorescent and/or colorimetric imaging technique. As further shown in FIG. 2, the cell medium 20 is placed on a top protective layer 28 of the flat panel detector 14—with the layer 22 providing protection to components of the detector.

According to one embodiment, one or more filters 30, 32 are positioned below the light source(s) 22, 24, 26 and/or directly beneath protective layer 28. The filters 30, 32 may be a combination of a narrow bandwidth filter, high pass and low pass filters 30, and/or a color (i.e., RGB) filter array 32—with the filters 30, 32 functioning to filter the light source emission from light source(s) 22, 24, 26, as is desirable for fluorescence imaging, to filter the light source emission from fluorescent light source 22 from the light generated by the cells in the sample 20 responsive to excitation of the fluorescent reagent by the light source 22, and/or to provide for the capture of color information in a colorimetric imaging technique to provide for the use of a color that has the highest absorbance for the employed stain.

Photons generated during the image acquisition pass through protective layer 28 and are absorbed by an array of photodetectors (i.e., photodiode/transistor array) that, according to an exemplary embodiment, is formed from/on an active amorphous silicon panel 34. While the array of photodetectors is described hereafter as being formed of an amorphous silicon 34, it is recognized that other suitable materials could instead be utilized/employed, including but not limited to: organic photodiode options, poly-silicon, crystal silicon, CMOS, and metal oxides (such as zinc oxide, zinc tin oxide, indium oxides, indium zinc oxides, indium gallium oxides, gallium zinc oxides, indium silicon zinc oxides, and indium gallium zinc oxides (IGZO)). As an example, in an embodiment where an organic photodiode is employed, the organic photodiode material may include an electron blocking layer including aromatic tertiary amines and polymeric aromatic tertiary amines, a mixture of a donor material containing a low bandgap polymer, and an acceptor material containing a fullerene material.

The photodiode/transistor array of the amorphous silicon panel 34 receives and converts photons into a plurality of representative image data values 36. Image data values 36 are received in analog form by interconnect electronics 38 and output therefrom as analog image data 40. Amorphous silicon panel 34 and interconnect electronics 38 are formed on silicon glass substrate 32 through semiconductor technology known in the art. For example, in fabrication, eleven layers of amorphous silicon, various metals, and insulators are deposited by plasma enhanced chemical vapor deposition ("PECVD"), sputtering and meniscus coating to form field effect transistors ("FETs"), diodes, interconnects, and contacts. Together, the protective layer 28, amorphous silicon panel 34, interconnect electronics 38, and glass substrate 42 form a flat panel detector 14.

With respect to the top protective layer 28, the layer is constructed to specifically accommodate placement of a cell medium 20 thereon and provide for accurate photon capture of the microbial cells. The protective layer 28 is thus formed so as to be transparent, sufficiently hard so as to resist scratching, and chemically resistant so as to allow wipe-down thereof with cleaning solvents after removal of a sample upon completion of a digital image acquisition. According to embodiments of the invention, the protective layer 28 may be constructed of glass, mylar, or another suitable thin, tough plastic, or may be a combination of both glass and plastic, where the plastic top sheet is a replaceable layer. In each embodiment, the surfaces of protective layer 28 can also be coated with a conductive polymer (PDOT) or indium tin oxide (ITO), for example, so as to prevent artifacts or damage that might occur if statically charged samples are placed on the detector.

According to an exemplary embodiment, the protective layer 28 is constructed as a "thin" layer having a thickness of ~25-75 um (e.g., 50 um) in order to prevent light spreading and maintain good spatial resolution, with the protective layer 28 providing for optimal transmission of photons therethrough so as not to degrade the modulation transfer function (MTF) of the amorphous silicon panel 34. The protective layer 28 also provides thermal isolation between the cell medium 20 and the amorphous silicon panel 34, which is desirable as it is recognized that local changes in temperature may affect the leakage current in the photodiodes, which can cause image artifacts. Additionally, the protective layer 28 may incorporate an angle discriminating film thereon to increase contrast and decrease crosstalk of light received by the flat panel detector 14.

Figure 3:
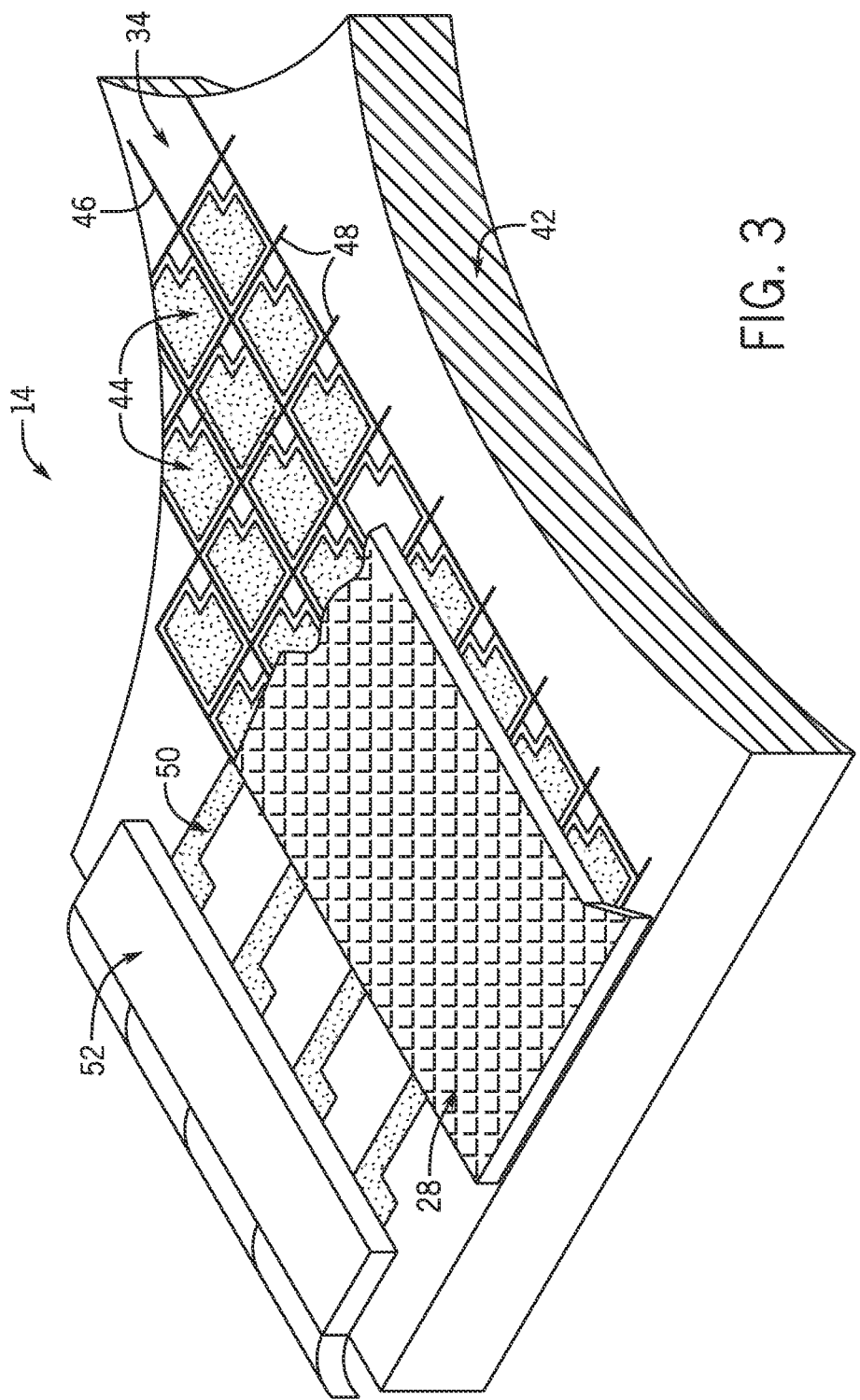
FIG. 3 is an elevated prospective view of the flat panel detector of FIG. 1 removed from a protective base portion, according to an embodiment of the invention.

Referring now to FIG. 3, an elevated prospective view of the flat panel detector 14 removed from base portion 16 (FIG. 1) is provided. As illustrated in FIG. 3, the top protective layer 28 covers the amorphous silicon panel 34, with the amorphous silicon panel being comprised of an array of photo cells or pixels 44 (active or passive) that convert light photons received on the detector surface during gel and blot imaging to electrical signals that are representative of the number of photons or the intensity of radiation impacting individual pixel regions of the detector surface. Row electrodes 36 and column electrodes 38 are connected to the pixels 44—with each pixel being generally defined at a row and column crossing, at which a row electrode or scan line 46 crosses a column electrode or data line 48. Contact fingers 50 are formed for receiving signals from the column electrodes 38, and contact leads 52 are provided for communicating the signals between the contact fingers 50 and readout electronics (not shown) that convert analog signals generated by the pixels 44 to digital values that can be processed, stored, and displayed following reconstruction of an image.

Figure 4:
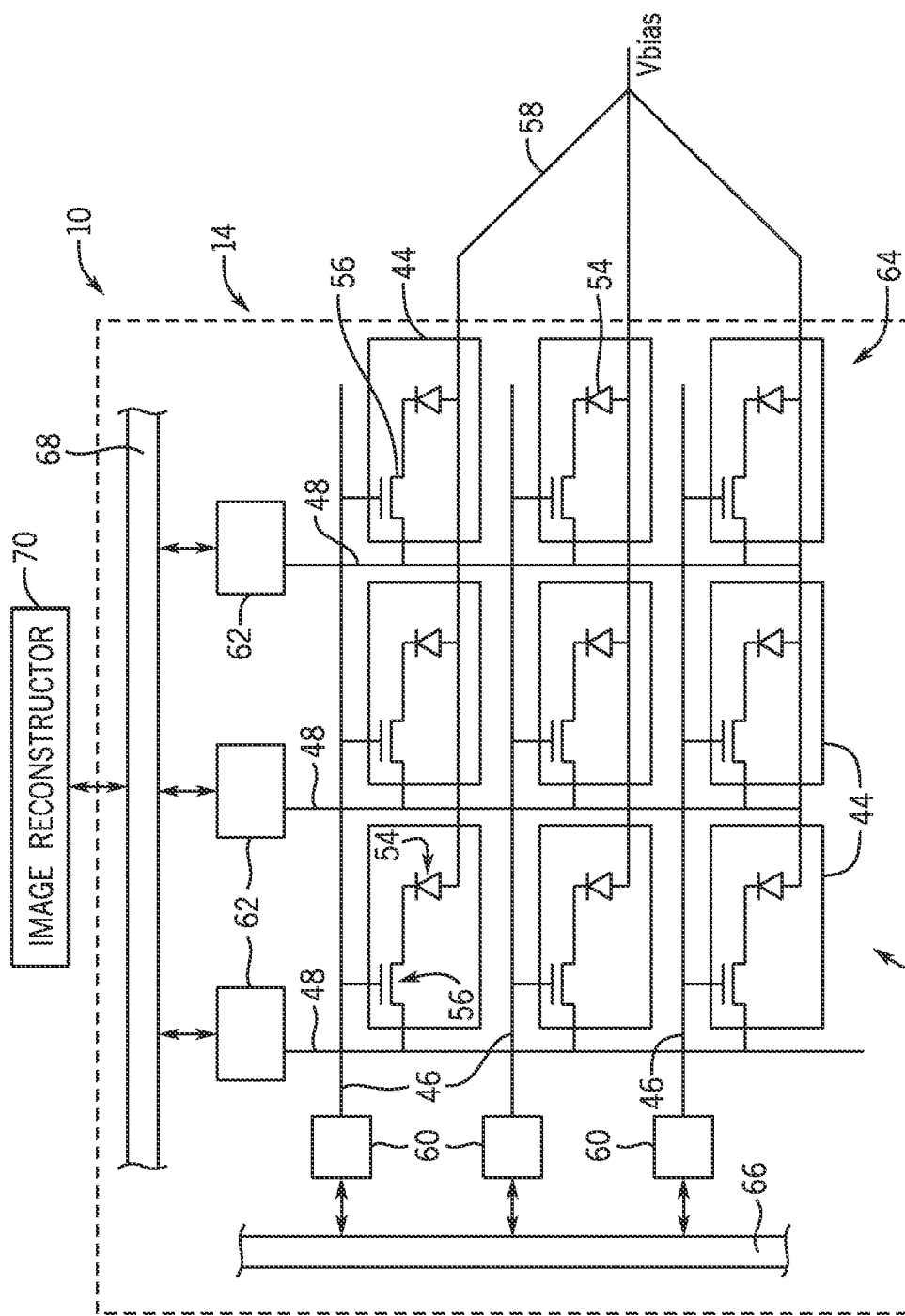
FIG. 4 is a schematic view of a photodetector array of the flat panel detector of FIG. 1, according to an embodiment of the invention.

As best illustrated in FIG. 4, the array elements or pixel regions 44 are organized in rows and columns 36, 38, with each pixel 44 including a photodiode 54 and associated thin film transistor 56 (TFT). The cathode of each diode 54 is connected to the source of the transistor 56, and the anodes of all diodes 54 are connected to a negative bias voltage 58. The gates of the transistors 56 in each row are connected together and the row electrodes 46 are connected to scanning electronics 60 (i.e., row drivers) described in further detail below. The drains of the transistors 56 in a column are connected together and an electrode of each column 48 is connected to readout electronics 62. In operation, the photodiodes 54 are biased by way of the negative bias voltage 48 and discharged at the appropriate time by way of transistors 56, with the transistors 56 controlling electrical discharge from the appropriate corresponding columns 48. The rows 46 and columns 48 of pixels 44 define an image matrix 64, having a height and width of desired size. For the flat panel detector 14, which is utilized for the imaging samples of microbial cells, the image matrix 64 may be constructed to have dimensions of approximately 40×40 cm, according to one embodiment, such that a large area cell medium of 20×20 cm may be placed thereon for performing of an image acquisition. The image matrix 64 may thus have an array of 2048 columns×2048 rows at 20-200 µm pitch, according to one embodiment.

Each of the rows and columns 46, 48 of pixels is coupled to a row bus 66 and column bus 68, respectively. The row bus 66 includes a plurality of conductors for enabling readout from various columns of the detector, as well as for disabling rows and applying a charge compensation voltage to selected rows, where desired. The column bus 68 includes additional conductors for reading out the columns while the rows are sequentially enabled. The row bus 66 is coupled to a series of row drivers 60, each of which commands enabling of corresponding row 46. Similarly, readout circuitry or electronics 62 is coupled to column bus 68 for reading out all columns 48. According to one embodiment, in response to sequential trigger signals from row drivers 60, all columns are simultaneously read out by readout electronics 62.

As mentioned above, a thin film transistor 56 is provided at each crossing location for each photodiode of each pixel region 44. As each row 46 is enabled by row drivers 60, signals from each photodiode 54 may be accessed via readout circuitry 62, and converted to digital signals for subsequent processing and image reconstruction—such as by way of an image reconstructor 70 provided separately from the flat panel imaging system 10. While image reconstructor 70 is shown separate from flat panel imaging system 10 in FIG. 4, it is recognized that in another embodiment the image reconstructor 70 could be incorporated into the flat panel imaging system 10.

Figure 5:
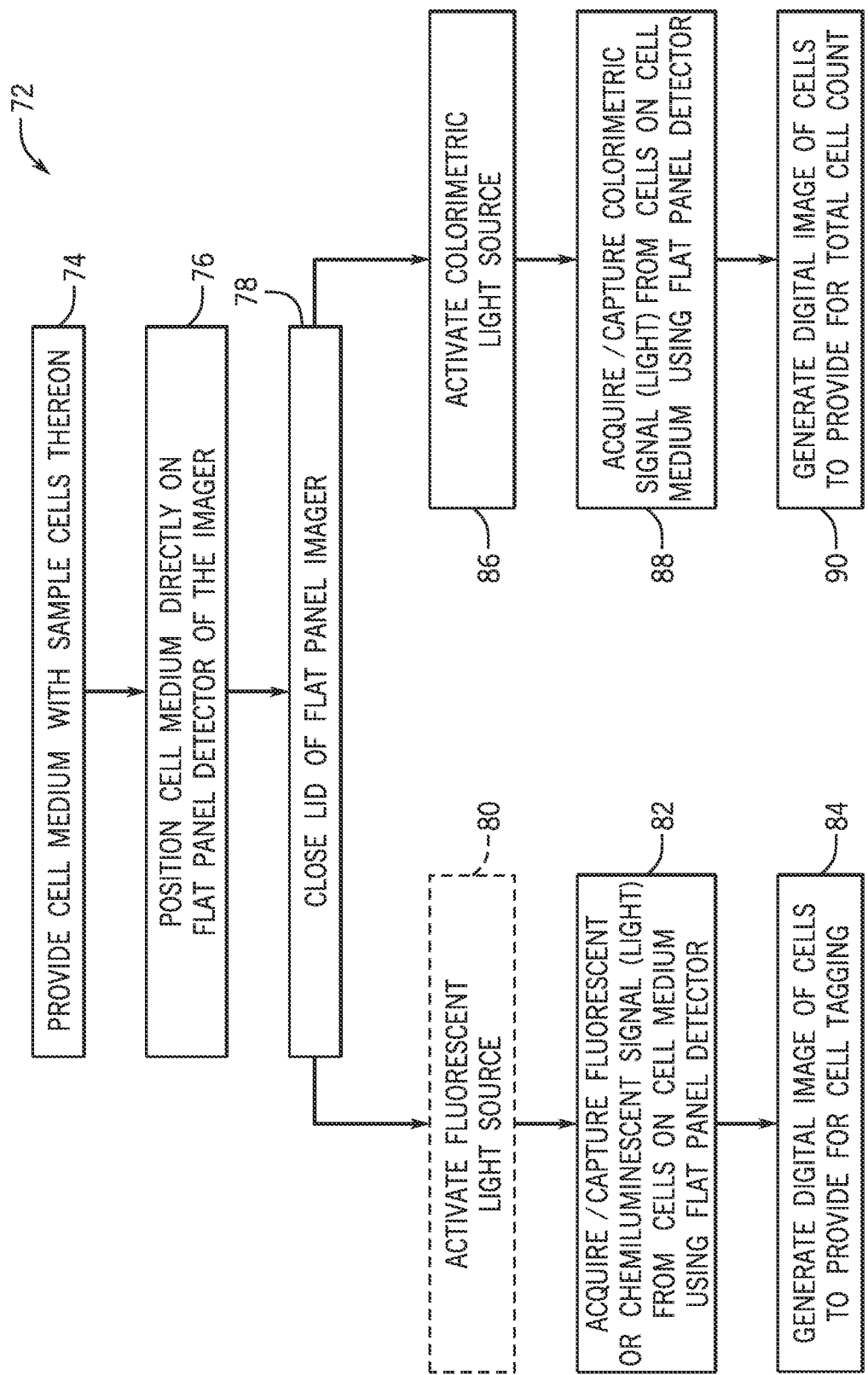
FIG. 5 is a flowchart illustrating a technique for digital image acquisition of a cellular sample using the flat panel imaging system of FIGS. 1-4, according to an embodiment of the invention.

Referring now to FIG. 5, and with continued reference back to FIGS. 1-4, a technique 72 of image generation for microbial cells provided on a cell medium is illustrated according to an embodiment of the invention. The technique 72 begins at STEP 74 with the providing of a cell medium 20 that includes microbial cells thereon. According to one embodiment, the cell medium 20 is a nutrient agar in a petri dish ("agar plate") on which bacterial cells have been dispersed and incubated under conditions that permit in situ bacterial replication. In providing the microbial cells on the cell medium 20, the cells are stained with an appropriate dye that provides for an image capture of the cells according to an imaging technique to be performed thereon—i.e., chemiluminescence, fluorescence and/or colorimetric imaging technique.

When a chemiluminescence imaging technique is to be performed, a dye/substrate molecule is provided that interacts with the microbial cells in order to generate a colored reaction product or luminescence (i.e., light) that will be detectable by the flat panel detector 14. When a fluorescence imaging technique is to be performed, the cells are fluorescently labeled to make them visible. A fluorescent reagent is utilized that causes a light to be emitted from the gel sample when the reagent is excited by a light source—such as light source 22 (UV or colored light source). The fluorescent reagent may be any of a number of stained nucleic acid gels that can be excited by a UV or colored light source. In one embodiment, the reagent may be ethidium bromide (EtBr), iridium bromide, or SYBR® Green, for example. In another embodiment, the reagent may be Texas Red or SYPRO® Ruby, for example. When a colorimetric imaging technique is to be performed, the cells on the cell medium 20 are prepared by applying soluble dyes (e.g., silver stain and Coomassie stains) to stain the cells.

Upon applying of a dye to the cells on cell medium 20, a completed sample of microbial cells on the cell medium 20 is provided at STEP 74. In a next step of technique 62, the cell medium 20 is then placed onto the flat panel detector 14 of the imager 10, as indicated at STEP 76. In one embodiment, the cell medium 20 is placed on the top protective layer 28 of the flat panel detector 14 such that it is in direct contact therewith. Accordingly, the cell medium 20 is positioned immediately adjacent to the amorphous silicon photodetector array 34 of the flat panel detector 14. Upon placement of the cell medium 20 on the flat panel detector 14, the lid 18 of the flat panel imaging system 10 is closed at STEP 78.

In an embodiment where a fluorescence imaging technique is performed, the technique continues by activating the light source 22 at STEP 80, as shown in phantom in FIG. 5. In particular, an output of light is provided from the light source 22 that excites the fluorescently labeled sample and causes light to be emitted from the cell sample 20, and this light is acquired/captured by the flat panel detector 14 at STEP 82. In an embodiment where a chemiluminescent imaging technique is performed, it is recognized that STEP 80 would not be performed, as the cells would produce a colored reaction product or luminescence signal without any excitation thereof from an external light source. Regardless of the technique performed, the light emitted from the sample 20 that is captured by the flat panel detector 14 is converted to electric charge, which is stored in the photodiodes 54 of the photodetector pixels 44 and subsequently read out by activating the thin film transistors 56 associated with the photodiodes 54, with the read-out time being adjustable as desired for properly detecting the light signal emitted from the cells.

The read-out of the charges stored in the photodiodes 54 is performed by read-out electronics 62 of the flat panel detector 14, which convert the charge to digital signals. The digital signals generated by the read-out electronics 62 may then be provided to an image reconstructor 70 for subsequent processing and generation of a digital image of the microbial cells in the sample, as indicated at STEP 84, with the digital image providing for the detection, enumeration, and identification of microbial cells. That is, locations on the flat panel detector 14 that receive a fluorescence or chemiluminescent signal would be tagged as containing a marked cell—with the marked cell, for example, being indicative of a cell that has responded to a particular treatment (e.g., application of medicine).

In addition to the performing of STEPS 80-84 for purposes of acquiring images of tagged/activated cells of interest—via either a fluorescence imaging technique or chemiluminescent imaging technique—technique 72 also provides for acquiring images of the microbial cells provided on cell medium via performing of a colorimetric imaging technique described in STEPS 86-90.

In performing the colorimetric imaging technique, an output of light is provided from the colorimetric light source 24 (i.e., white light source) at STEP 86. Light absorption through the cell medium 20 is acquired/captured by the flat panel detector 14 at STEP 88 and converted to electric charge, which is stored in the photodiodes 54 of the photodetector pixels 44 and subsequently read out by activating the thin film transistors 56 associated with the photodiodes 54. The read-out of the charges stored in the photodiodes 54 is performed by read-out electronics 62 of the flat panel detector 14, which convert the charge to digital signals. The digital signals generated by the read-out electronics 62 may then be provided to an image reconstructor 70 for subsequent processing and generation of a digital image of the microbial cells in the sample, as indicated at STEP 90, with the digital image providing for the detection, enumeration, and identification of microbial cells that enables a call counting of cells on the cell medium 20 to be performed. That is, locations on the flat panel detector 14 that receive a colorimetric/absorbance signal would be indicative of a location where a cell is present—as compared to locations where a cell is not present—so as allow for an estimation of a total cell count.

It is recognized that the performing of the fluorescence/chemiluminescent imaging technique (STEPS 80-84) and the performing of the colorimetric imaging technique (STEPS 86-90) may be performed in a desired order by an operator of the flat panel imaging system. That is, the fluorescence/chemiluminescent imaging technique may be performed prior to the colorimetric imaging technique or, conversely, the colorimetric imaging technique may be performed prior to the fluorescence/chemiluminescent imaging technique. However, regardless of the order in which the specific imaging techniques are performed, it is recognized that the flat panel imaging system 10 beneficially provides for the performing of both techniques using the same imaging system. With regard specifically to the use of the flat panel imaging system 10 for the detection, enumeration, and identification of microbial cells, this allows for both an estimation of a total cell count and an identification of cells that are tagged/activated responsive to a specific treatment in a quick and efficient manner using the capabilities of the flat panel imaging system 10.

Figure 6:
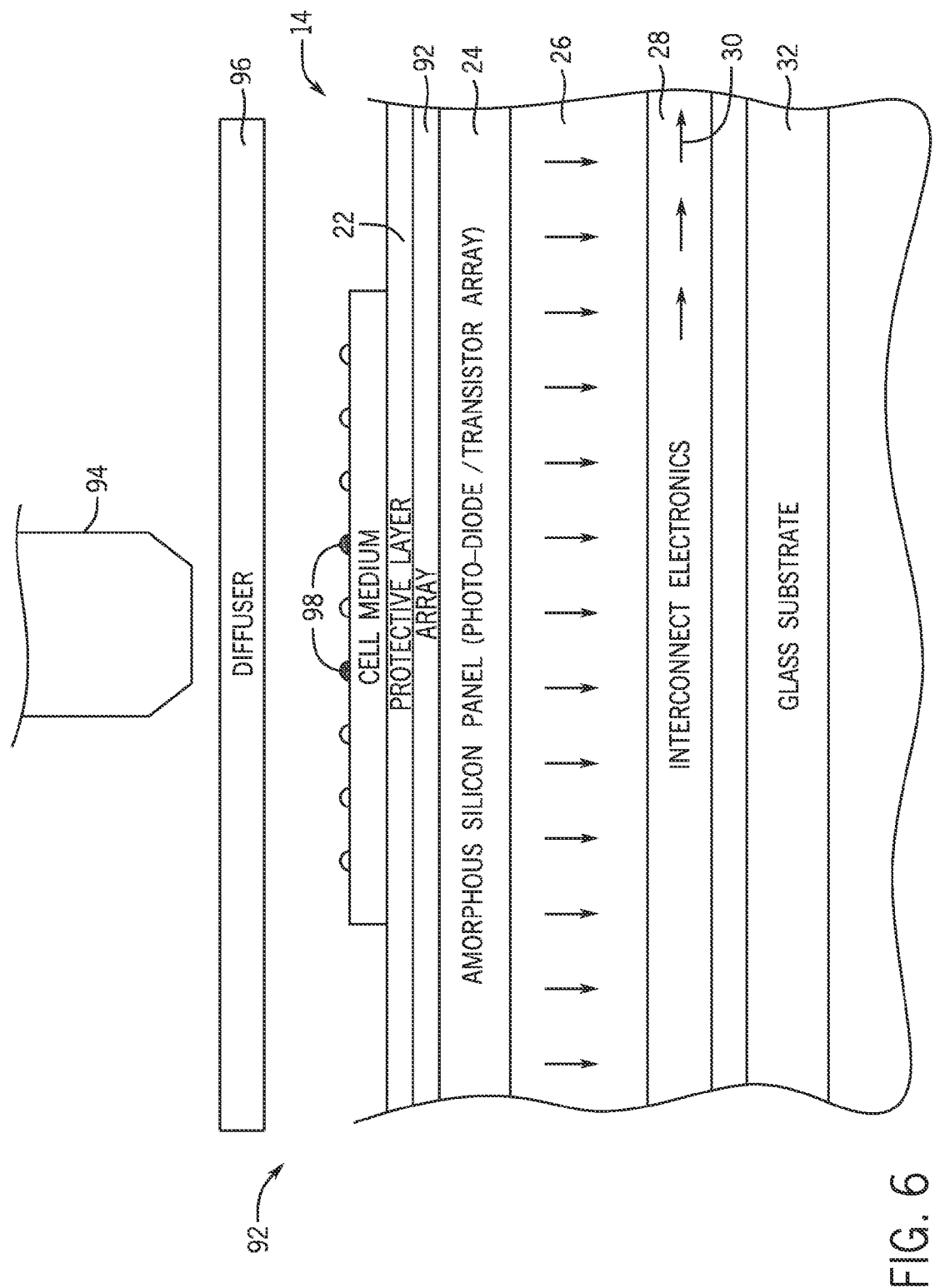
FIG. 6 is an exploded sectional view of a flat panel imaging system, according to an embodiment of the invention.

Referring now to FIG. 6, a flat panel imaging system 92 is shown according to another embodiment of the invention. The structure of the flat panel imaging system 92 is similar to that shown and described in FIGS. 1-4 but further includes a microscope 94 that is integrated therewith that provides for high resolution imaging of tagged cells. The microscope 94 is positioned above the cell medium 20 and is movable to various locations so as to provide for viewing of a desired area on the cell medium. A diffuser 96 may also be positioned between the microscope 94 and the cell medium 20 to soften the image of the cells acquired via the microscope 94. In operation, the flat panel imaging system 92 may first be operated to perform a fluorescence or chemiluminescent imaging technique (as described in FIG. 5) that serves to activate or tag cells of interest on the cell medium 20—indicated at 98—such as cells being tagged that have responded to a particular treatment (e.g., application of medicine). The microscope 94 in flat panel imaging system 92 is then employed to provide high resolution imaging of these tagged cells 98—so as to enable further analysis of the cells.

Referring now to FIG. 7, flat panel imaging system 92 is shown according to another embodiment of the invention. That is, in addition to including a microscope 94 that enables high resolution imaging of a desired area on the cell medium, such that tagged cells of the microbial culture can be further analyzed, the flat panel imaging system 92 also includes a piezoelectric device or element 100 that can be attached to the flat panel detector 14 to allow for the acquisition of repeated images with sub-pixel displacement. That is, the piezoelectric element 100 functions to cause a selective lateral shifting of the photodetectors formed from/on the amorphous silicon panel 34, such that each of the images captured by the flat panel imaging system 92 also includes a small, lateral shift as compared to each other image that is captured. The redundant image data can purposely be made to have these small, known lateral shifts introduced by the piezoelectric element 100. The small lateral shifts that are less that a pixel in size are referred to as sub-pixel shifts and function to generate the necessary images needed for use in super resolution enhancement of the captured images, such as might be performed by the image reconstructor 70 (FIG. 4). The small lateral shifts of the images permits roughly a doubling of the effective image resolution based upon the sub-pixel sampling—such that the effective resolution of the flat panel detector 14 can be improved to a level of 1-5 µm.

Beneficially, embodiments of the invention thus provide a flat panel imaging system having a flat panel detector that functions as a matrix-based light sensor array, with the flat panel detector being composed of an array of pixels each comprising a photodiode-transistor pair that detect/capture light emitted from a cell medium including microbial cells according to an imaging process that utilizes a chemiluminescence, fluorescence and/or colorimetric detection technique. Each pixel may be sized so as to provide for reasonable spatial resolution in capturing light from the sample, with pixels down to a size of 20 microns being included in the flat panel detector. The flat panel imaging system provides demanding performance in terms of sensitivity, dynamic range, exposure time, and quantum efficiency, and collects photons directly and efficiently from the sample, which eliminates costly high-efficiency imaging optics used with small cooled CCD image sensors and greatly improves the workflow associated with traditional film—with image capture times of less than 10 seconds (e.g., 6 seconds) being achievable. The fast acquisition speed enables the use of software to obtain virtually infinite dynamic range, reducing time and effort for each experiment. Of still further benefit, the flat panel imaging system also can provide a quasi-stationary image with reasonable signal-to-noise ratio, which is superior to a scan method. The flat panel imaging system also offers compactness for portability.

Additionally, the flat panel imaging system beneficially provides for the performing of chemiluminescence, fluorescence, and colorimetric detection techniques using the same imaging system. With regard specifically to the use of the flat panel imaging system for the detection, enumeration, and identification of microbial cells, this allows for both an estimation of a total cell count and an identification of cells that are tagged/activated responsive to a specific treatment in a quick and efficient manner using the capabilities of the flat panel imaging system. According, the need to perform a separate cell count (either manually by eye or thru a separate electronic/automated method) is eliminated, thereby increasing process efficiencies.

Therefore, according to one embodiment, a flat panel imaging system for imaging cells provided on a cell medium includes a housing having a base portion and a lid that collectively form a closed environment to exclude external sources of light from entering the housing and a flat panel detector encased in the base portion, the flat panel detector comprising an array of pixels each including a photodiode and transistor that convert photons received thereby to electrical signals that are representative of the photons impacting individual the respective pixel. The flat panel imaging system also includes a first light source configured to illuminate the cells on the cell medium with a light that excites at least a portion of the cells and causes those cells to generate photons that are captured by the array of pixels and a second light source configured to illuminate the cells on the cell medium with a light different from the light from the first light source, the light from the second light source providing for a capturing of photons by the array of pixels representative of photons transmitted through the cells on the cell medium.

According to another embodiment, a method for detecting and enumerating cells in a cell culture using a flat panel imaging system includes providing a cell medium having a plurality of cells thereon and placing the cell medium on a flat panel detector of a flat panel imaging system, the flat panel detector comprising an array of photodiodes and transistors that collect light generated from or transmitted through the cell medium. The method also includes collecting light emitted by cells on the cell medium responsive to an excitation of the cells achieved via one of a chemiluminescence imaging technique and a fluorescence imaging technique, the light emitted by the cells being collected by the array of photodiodes of the flat panel detector and converted to electric charges to generate a first set of light data. The method further includes processing the first set of light data to generate a first digital image of the cells, collecting light transmitted through the cells on the cell medium responsive to illumination of the cells by a light source integrated into the flat panel imaging system and via the array of photodiodes of the flat panel detector and converted to electric charges to generate a second set of light data, and processing the second set of light data to generate a second digital image of the cells.

According to yet another embodiment, a flat panel imaging system for detecting and enumerating cells microbial cells provided on a cell medium includes a housing having a base portion and a lid that collectively form a closed environment to exclude external sources of light from entering the housing and a flat panel detector encased in the base portion, the flat panel detector comprising an array of pixels each including a photodiode and transistor that convert photons received thereby to electrical signals that are representative of the photons impacting individual the respective pixel. The flat panel imaging system also includes a fluorescent light source configured to illuminate the cells on the cell medium so as to excite at least a portion of the cells and cause those cells to generate photons that are captured by the array of pixels and a white light source configured to illuminate the cells on the cell medium, with photons transmitted through the cells being captured by the array of pixels. The flat panel imaging system further includes an image reconstructor configured to process the electrical signals that are representative of the photons received by the array of pixels so as to provide for generation of a digital image of the cells on the cell medium, wherein the image reconstructor is configured to generate a first image of the microbial cells that captures cells that are excited responsive to illumination with the fluorescent light, with the first image tagging locations at which photons generated by cells excited responsive to illumination with the fluorescent light as containing a marked cell, and generate a second image of the microbial cells that captures cells through which photons are transmitted when illuminated by the white light source, the second image providing a total cell count of the microbial cells on the cell medium.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A flat panel imaging system for imaging cells provided on a cell medium, the flat panel imaging system comprising:
   a housing including a base portion and a lid that collectively form a closed environment to exclude external sources of light from entering the housing;
   a flat panel detector encased in the base portion, the flat panel detector comprising an array of pixels each including a photodiode and transistor that convert photons received thereby to electrical signals that are representative of the photons impacting individual the respective pixel;
   a first light source configured to illuminate the cells on the cell medium with a light that excites at least a portion of the cells and causes those cells to generate photons that are captured by the array of pixels; and
   a second light source configured to illuminate the cells on the cell medium with a light different from the light from the first light source, the light from the second light source providing for a capturing of photons by the array of pixels representative of photons transmitted through the cells on the cell medium.

2. The flat panel imaging system of claim 1 wherein the photons generated by or transmitted through the cells on the cell medium result from one of a chemiluminescence, fluorescence, or colorimetric imaging technique.

3. The flat panel imaging system of claim 1 wherein the first light source comprises a fluorescent light source configured to output light that excites a fluorescent reagent with which the cells are labeled, so as to cause the at least a portion of the cells to generate photons; and wherein the second light source comprises a white light source.

4. The flat panel imaging system of claim 1 further comprising one or more filters positioned between the cell medium and the first and second light sources, the filters comprising at least one of a narrow bandwidth filter, high pass and low pass filters, and a color filter array.

5. The flat panel imaging system of claim 1 further comprising a transparent protective layer positioned over the array of pixels to provide protection thereto and provide for transmission of photons there through to the array of pixels, with the cell medium being place directly on the transparent protective layer.

6. The flat panel imaging system of claim 1 further comprising a microscope integrated into the flat panel imaging system.

7. The flat panel imaging system of claim 1 further comprising a piezoelectric element attached to the flat panel detector that causes a lateral shifting of the array of pixels.

8. The flat panel imaging system of claim 7 further comprising an image reconstructor configured to process the electrical signals that are representative of the photons received by the array of pixels so as to provide for generation of a digital image of the cells on the cell medium, and wherein the lateral shifting of the array of pixels provides for a sub-pixel image shift between each of a number of images generated by the image reconstructor, thereby providing redundant imaging data between the images.

9. The flat panel imaging system of claim 8 wherein the image reconstructor is configured to perform a super resolution enhancement of the generated images based on the redundant imaging data.

10. The flat panel imaging system of claim 9 wherein the super resolution enhancement provides an effective resolution of 1-5 μm for the flat panel detector.

11. The flat panel imaging system of claim 1 wherein the flat panel detector is sized to accommodate placement of a cell medium of 20×20 cm thereon.

12. A method for detecting and enumerating cells in a cell culture using a flat panel imaging system, the method comprising:
providing a cell medium having a plurality of cells thereon;
placing the cell medium on a flat panel detector of a flat panel imaging system, the flat panel detector comprising an array of photodiodes and transistors that collect light generated from or transmitted through the cell medium;
collecting light emitted by cells on the cell medium responsive to an excitation of the cells achieved via one of a chemiluminescence imaging technique and a fluorescence imaging technique, the light emitted by the cells being collected by the array of photodiodes of the flat panel detector and converted to electric charges to generate a first set of light data;
processing the first set of light data to generate a first digital image of the cells;
collecting light transmitted through the cells on the cell medium responsive to illumination of the cells by a light source integrated into the flat panel imaging system, the light transmitted through the cells being collected by the array of photodiodes of the flat panel detector and converted to electric charges to generate a second set of light data; and
processing the second set of light data to generate a second digital image of the cells.

13. The method of claim 12 further comprising tagging locations at which light emitted by cells responsive to one of the chemiluminescence imaging technique and the fluorescence imaging technique is received by the flat panel detector as containing a marked cell, the tagged locations containing a marked cell being determined from the first digital image of the cells.

14. The method of claim 13 further comprising obtaining a high resolution image of the marked cells using a microscope integrated into the flat panel imaging system.

15. The method of claim 12 further comprising determining a total cell count of the cells on the cell medium from the second digital image of the cells.

16. The method of claim 12 wherein collecting light emitted by cells on the cell medium responsive to an excitation of the cells achieved via one of a chemiluminescence imaging technique and a fluorescence imaging technique comprises illuminating the cells on the cell medium using a fluorescent light source integrated into the flat panel imaging system and that excites a fluorescent reagent with which the cells are labeled.

17. The method of claim 16 further comprising performing one or more filtering operations during an image acquisition, the one or more filtering operations including at least one of:
filtering the light from the fluorescent light source from the light emitted by the cells, so to provide for collection of only the light emitted by the cells by the array of photodiodes of the flat panel detector; and
filtering light collected by the array of photodiodes to provide for the capture of color information in a colorimetric imaging technique.

18. The method of claim 12 wherein collecting light transmitted through the cells on the cell medium responsive to illumination of the cells by a light source further comprises transilluminating the gel sample using a white light source.

19. The method of claim 12 further comprising:
activating a piezoelectric element coupled to the flat panel detector to cause a sub-pixel lateral shift thereof during acquisition of a first set of light data from which a respective first digital image is generated;
comparing each of a number of generated first digital images that include a sub-pixel lateral shift, thereby providing redundant imaging data between the images; and
performing a super resolution enhancement of the generated first digital images based on the redundant imaging data.

20. A flat panel imaging system for detecting and enumerating cells microbial cells provided on a cell medium, the flat panel imaging system comprising:
a housing including a base portion and a lid that collectively form a closed environment to exclude external sources of light from entering the housing;
a flat panel detector encased in the base portion, the flat panel detector comprising an array of pixels each including a photodiode and transistor that convert photons received thereby to electrical signals that are representative of the photons impacting individual the respective pixel;
a fluorescent light source configured to illuminate the cells on the cell medium so as to excite at least a portion of the cells and cause those cells to generate photons that are captured by the array of pixels;

a white light source configured to illuminate the cells on the cell medium, with photons transmitted through the cells being captured by the array of pixels; and an image reconstructor configured to process the electrical signals that are representative of the photons received by the array of pixels so as to provide for generation of a digital image of the cells on the cell medium, wherein the image reconstructor is configured to:

generate a first image of the microbial cells that captures cells that are excited responsive to illumination with the fluorescent light, the first image tagging locations at which photons generated by cells excited responsive to illumination with the fluorescent light as containing a marked cell; and generate a second image of the microbial cells that captures cells through which photons are transmitted when illuminated by the white light source, the second image providing a total cell count of the microbial cells on the cell medium.

* * * * *